United States Patent [19]

Chang et al.

[11] Patent Number: 4,563,354

[45] Date of Patent: Jan. 7, 1986

[54] OIL-IN-WATER EMULSION FOR PARENTERAL ADMINISTRATION

[75] Inventors: Stephen S. Chang, E. Brunswick, N.J.; Lars Lindmark, Stockholm, Sweden

[73] Assignee: Kabivitrum AB, Stockholm, Sweden

[21] Appl. No.: 545,752

[22] Filed: Oct. 26, 1983

[51] Int. Cl.$^4$ .................... A61K 35/78; A61K 31/23
[52] U.S. Cl. ................... 424/195.1; 514/552; 514/938; 514/975
[58] Field of Search ............ 424/195, 312, 195.1; 514/552, 975, 938

[56] References Cited

U.S. PATENT DOCUMENTS

| | | | |
|---|---|---|---|
| 1,001,247 | 8/1911 | Baer et al. | 260/403 |
| 1,667,767 | 5/1928 | Bollmann | 260/403 |
| 2,727,046 | 12/1955 | Scholfield et al. | 260/403 |
| 2,945,869 | 7/1960 | Meyer et al. | 424/312 |
| 2,977,283 | 3/1961 | Meyer et al. | 424/312 |
| 3,169,094 | 2/1965 | Johannes | 424/312 |
| 4,101,673 | 7/1978 | Chang | 424/312 |
| 4,235,793 | 11/1980 | Betzing | 260/403 |

FOREIGN PATENT DOCUMENTS 43018  1/1982  European Pat. Off. .

*Primary Examiner*—Allen J. Robinson
*Assistant Examiner*—John W. Rollins, Jr.
*Attorney, Agent, or Firm*—Donald E. Egan

[57] ABSTRACT

An emulsifier adapted for use in a nutritive oil-in-water emulsion suitable for parenteral administration is produced by extracting vegetable lecithin with alkyl alcohols having from 1 to 3 carbon atoms, or mixtures thereof, followed by fractional precipitation at specific temperatures and concentrations effective to cause the removal of toxic materials. The alcohol soluble phospholipid fraction produced by the process contains an increased level of phosphatidyl choline and reduced levels of phosphatidyl ethanolamine, inositol phospholipids, phosphatidic acid and glycolipids.

20 Claims, 6 Drawing Figures

OIL-IN-WATER EMULSION FOR PARENTERAL ADMINISTRATION

BACKGROUND OF THE INVENTION

Soybean phospholipids have been used as emulsifiers in various oil-in-water emulsions. Such soybean phospholipids are particularly useful for the emulsification of soybean oil and similar vegetable oils, as compared to other emulsifiers such as phospholipids derived from egg and the like, because the soybean phospholipids produce more stable emulsions of soybean oil-in-water.

Naturally occurring phopholipids can be obtained from either egg yolks or soybeans or other vegetable sources, and while there are chemical similarities among the phospholipids, in each case they consist of a mixture of chemically different phospholipids, with phosphatidyl choline, phosphatidyl ethanolamine, and phosphatidyl inositol being predominant components thereof. Emulsions used for parenteral nutrition produced from soybean phospholipids could be advantageous in that they are free from cholesterol. The soybean phopholipids have an added advantage in that their fatty acid composition is more similar to that of the soybean oil used in the emulsion than that of the egg phospholipids. Similar fatty acid compositions are claimed to produce more stable emulsions. Although a number of prior art workers have advocated the use of soybean-based phospholipids as emulsifiers for oil-in-water emulsions for parenteral feeding, the emulsions prepared from soybean phospholipid emulsifiers have proved to have undesirable properties and some soybean phospholipid fraction emulsifiers have proved to be toxic for these purposes.

The present invention is based on the discovery that certain alcohol-soluble fractions of vegetable lecithin are suitable for use as emulsifiers for oil-in-water emulsions and that the resulting oil-in-water emulsion made with the alcohol-soluble fractions are well tolerated when used for parenteral nutrition.

In particular, it has been found that a non-toxic alcohol-soluble fraction of soybean phospholipids is produced by extracting soybean lecithin with alcohol, wherein the insolubles are removed from the extraction by cooling the alcohol-soluble lecithin mixture at a specific alcohol concentration to a reduced temperature followed by filtration. The resulting alcohol-soluble fraction has a markedly reduced level of toxic components found in the alcohol-insoluble fractions and which exist in the natural soybean lecithin prior to fractionation.

The alcohol-soluble fraction which finds great utility as an emulsifier for oil-in-water parenteral nutrition emulsions can be characterized to some extent by phospholipids appearing therein. It has been found that the alcohol-soluble fraction which is useful as an emulsifier has a relatively low concentration of inositol phospholipids, a relatively low concentration of phosphotidyl ethanolamine and a relatively high concentration of phosphatidyl choline. A component characterized as phosphatidic acid, containing small amounts of phosphatidyl serine (referred to hereafter as PA), shown as a peak PA on the HPLC spectra, is also removed. Moreover, it has been found that the alcohol-soluble fractions of the present invention have a reduced concentration of saturated fatty acids (i.e., C16:0 and C18:0) and an increased concentration of polyunsaturated fatty acids (i.e., C18:2). Furthermore, it has been found that the alcohol soluble fractions of the present invention have a reduced concentration of glycolipids.

BRIEF DESCRIPTION OF THE INVENTION

Briefly, the invention contemplates the preparation of an emulsifier adapted for use in nutritive oil-in-water emulsions wherein the emulsifier is derived from vegetable lecithin, preferably the vegetable lecithin from the same source as the oil used in the oil-in-water emulsion. In the first step, the vegetable lecithin is extracted with a lower alkyl alcohol having from about 1 to 3 carbon atoms in a molecule or mixtures of such alcohols at temperatures which may vary from −20° to 50° or more centigrade. The resulting alcohol soluble material is then subject to a fractional precipitation at specific temperatures and concentrations which are effective to cause removal of materials which are toxic when used in oil-in-water emulsions.

The invention may be better understood by reference to the drawings in which.

TABLE I

Figure 6:
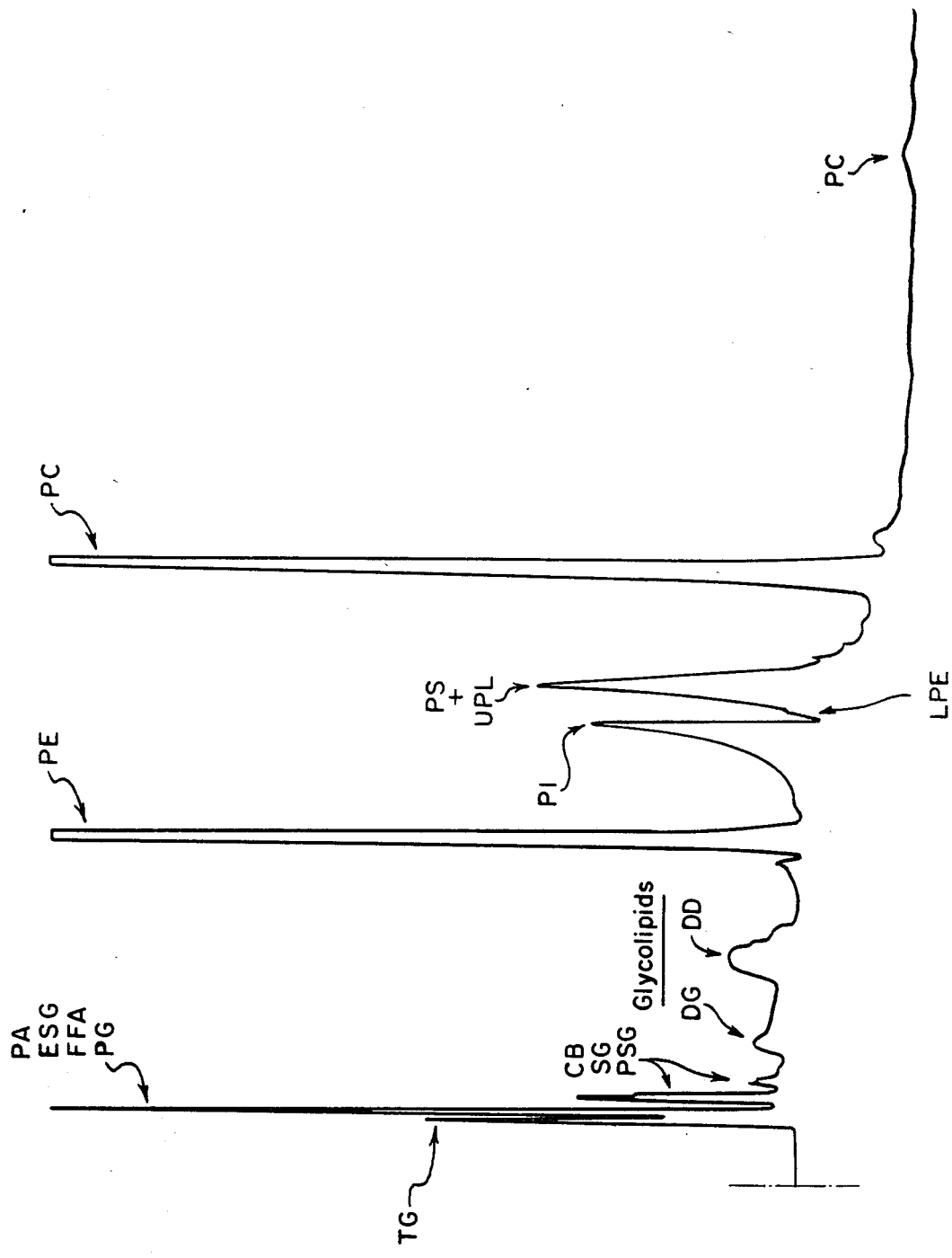
FIG. 6 is a high performance liquid chromatography spectra of the same commercial sample of granular soybean lecithin shown in FIG. 1, but on a larger scale, with the peaks identified by symbols, the key to which as shown in Table 1 below.

| KEY FOR FIG. 6 |
| --- |
| TG — Triglycerides |
| PA — Phosphatidic Acid |
| ESG — Esterified Steryl Glucosides |
| FFA — Free Fatty Acids |
| PG — Phosphatidyl Glycerol |
| CB — Cerebrosides |
| SG — Steryl Glucosides |
| PSG — Phytosphingosine |
| DG — Diphosphatidyl Glycerol |
| DD — Digalactosyl Diglyceride |
| PE — Phosphatidyl Ethanolamine |
| PI — Phosphatidyl Inositol |
| LPE — Lyso-PE |
| PC — Phosphatidyl Choline |
| LPC — Lyso-PC |

DETAILED DESCRIPTION OF THE INVENTION

In carrying out the process of the present invention it is desired to start with commercial vegetable lecithin. A suitable soybean lecithin is commercially available under the trade name ALCOLEC from American Lecithin Co., among other sources. Other vegetable lecithin, such as those from sunflower oil, corn oil and peanut oil may also be used.

The prefered starting material is the so-called "wet gum" obtained in the normal, commercial water degumming of crude soybean oil. "Wet gum" lecithin has not been subjected to the thermal deterioration that occurs during the thermal dehydration of "wet gum". Preferably, the free sugars are removed from the starting commercial soybean phospholipids prior to the application of the low temperature fractional separation of the present invention. The method described in U.S. Pat. No. 2,727,046 issued Dec. 13, 1955 may be used for this purpose. Alternatively, granular lecithin or fluid lecithin may be used as the starting material.

A preliminary purification of the lecithin is generally preferred, in order to remove some impurities. The lecithin is dissolved in a solvent, such as hexane, and the lecithin precipitated therefrom through the use of acetone. For example, the lecithin may be dissolved in hexane (about 2 liters of hexane per kilo of lecithin) and then precipitated by pouring the lecithin-hexane solution into five times the volume of acetone.

THE EXTRACTION PROCESS

The purified lecithin is next extracted with an alcohol, preferably at temperature ranging from $-20°$ C. to slightly elevated temperature, to extract the alcohol-soluble portion of the lecithin. The examples which follow illustrate the use of ethyl alcohol, which is preferred, but lower alkyl alcohols having up to 3 carbon atoms or mixtures of such alcohols may also be used.

Although the alcohol extraction process may be carried out under many different conditions, it has been found that use of 4 liters of 95% ethyl alcohol or absolute ethyl alcohol may be used to extract one kilo (after hexane-acetone purification) of lecithin at 50° C. for 5 minutes produces useful results. The extraction may be repeated multiple times. The present invention also contemplates the use of several extractions where a relatively small quantity of alcohol is used.

It is generally preferred to keep the extraction conditions mild with respect to temperatures and times. While temperatures higher than 50° C. may be used, it is generally desired to keep the temperatures relatively low in order to avoid the possibility of oxidizing or decomposing any components of the alcohol-soluble fractions. The operations described in the process described above may be carried out under nitrogen or other inert gases in order to minimize the possibility of oxidation of the components of the soybean phospholipid.

The number of extractions used may be varied as discussed. It is contemplated that most of the soluble materials are removed by 3 or 4 extractions and that additional extractions do not appear worthwhile.

A sample of granular commercial lecithin was repeatedly extracted with ethanol at $-20°$ C., up to 7 times. The results shown below in Table II indicated that even though a considerable amount of material can be extracted, even up to the seventh extraction, the yield of $-20°$ C., 1:5, ethanol soluble fraction is small after the fourth extraction.

TABLE II

YIELD OF REPEATED EXTRACTION OF GRANULAR LECITHIN

| Extraction No. | Yield before Separation at $-20°$ C., 1:5, g. | Yield After Separation at $-20°$ C., 1:5 | |
|---|---|---|---|
| | | g. | % |
| 1 | 36.0 | 18.0 | 3.6 |
| 2 | 25.5 | 10.0 | 2.0 |
| 3 | 17.5 | 8.5 | 1.7 |
| 4 | 18.0 | 5.0 | 1.6 |
| 5 | 11.0 | 3.0 | 0.6 |
| 6 | 14.1 | 3.0 | 0.6 |
| 7 | 15.5 | 3.5 | 0.7 |

ALTERNATIVE EXTRACTION PROCESS CONDITIONS

The foregoing description is based on the use of 95% ethyl alcohol as the extracting medium. Those skilled in the art will be aware that other lower alkyl alcohols may be used to extract similar or identical phospholipids. To this end, those skilled in the art will be aware that isopropyl alcohol may be substituted for all of part of the ethyl alcohol and that other mixtures of lower alkyl alcohols may be used. The relative volume of extracting alcohol used may be varied over substantial ranges, depending upon the precise alcohol or alcohol mixture employed. The quantities of alcohol described above and illustrated by the examples have shown to be useful, but the invention is not restricted to the use of these precise volumes. Some of the examples of extraction as given in Table III illustrate the possibility of using granular lecithin, as starting material, and absolute ethanol and 95% ethanol as the solvent at different temperatures and different solvent: material ratio.

TABLE III

EXTRACTION OF GRANULAR LECITHIN SOYBEAN PHOSPHATIDES WITH DIFFERENT SOLVENT RATIOS

| Solvent Used | Ratio Solvent:SP | Temp. of Extraction °C. | # of Extraction | Total Yield |
|---|---|---|---|---|
| Ab. ethanol | 1:1 | $-20$ | 8 | 11.1 |
| Ab. ethanol | 8:1 | $-20$ | 1 | 2.6 |
| Ab. ethanol | 8:1 | $-20$ | 1* | 5.3 |
| Ab. ethanol | 1:1 | $-20$ | 4 | 8.1 |
| Ab. ethanol | 2:1 | $-20$ | 8 | 14.4 |
| Ab. ethanol | 2:1 | $-20$ | 6 | 11.7 |
| Ab. ethanol | 2:1 | $-20$ | 4 | 10.7 |
| Ab. ethanol | 2:1 | 0 | 7 | 18.3 |
| Ab. ethanol | 2:1 | 0 | 1 | 7.9 |
| 95% ethanol | 4:1 | 50 | 6 | 12.0 |
| 95% ethanol | 4:1 | 50 | 2 | 7.1 |

*Extracted with 1:1, then extracted with 7:1

THE FRACTIONATION PROCESS

The filtrates from the alcohol extraction step are combined and chilled to produce a precipitate. Again the conditions under which the precipitation is accomplished may vary over substantial ranges. It has been found that chilling the combined filtrate to a temperature of about $-20°$ C. for about 24 hours produces useful results. After the first chilling step, the solids are separated from the soluble portion by filtration. The insoluble matter is discarded and the filtrate is further processed.

The filtrate from the first alcohol chilling step is freed of solvent under vacuum and again dissolved in alcohol. Although the conditions under which the second dissolution takes place may vary over a wide scope, it has been found that the filtrate can be dissolved in 5 aliquots of 95% alcohol. The extract can be concentrated to a concentration of 1 part of phospholipids in 5 parts of alcohol in one step and then subject the concentrated solution to low temperature fractional precipitation. The resulting solution is chilled in order to precipitate any insolubles. It has been found that holding the solution at $-20°$ C. for 24 hours produces useful results. The precipitate is removed by filtration and discarded.

The filtrate is again treated to remove solvent (by vacuum) and the residue is precipitated from acetone to yield the alcohol-soluble soybean phospholipids fraction.

The chilling temperature and times described above and illustated in the examples provide useful results, but the invention is not limited thereto. If lower chilling temperatures are used it is advantageous to increase the volume of extracting alcohol in order to improve the low temperature filtration and to increase the yield.

FRACTIONATION AT DIFFERENT SOLVENT TO PHOSPHOLIPID RATIOS

It is generally preferred to use a relatively high ratio of solvent to phospholipids, in order to increase the yield.

To demonstrate the advantages of high solvent ratios, the following experiments were run:

A sample of granular lecithin was reprecipitated from acetone and separated into alcohol-soluble and alcohol-insoluble fractions by extractions with 95% ethanol at room temperature to yield 53.6% as an alcohol-soluble fraction and 41.4% as an alcohol-insoluble fraction. Portions of the alcohol-soluble fraction were dissolved at different concentrations in 95% ethanol and stored at $-20°$ C. for 24 hours. The results shown in Table IV below indicated that the lower the ratio of solvent to phospholipids, the lower the yield of the alcohol-soluble fraction.

HPLC analysis of the different alcohol-soluble fractions showed a decrease in PE and PA as the ratio of solvent to phospholipids is decreased.

TABLE IV

YIELD OF ALCOHOL SOLUBLE FRACTION AS EFFECTED BY RATIO OF SOLVENT
($-20°$ C. FOR 24 HOURS)

| Sample Concentration SP:Solvent | Alcohol-Insoluble Fraction | Alcohol-Soluble Fraction* |
|---|---|---|
| 1:40 | 9.5 | 31.9 |
| 1:30 | 12.5 | 28.8 |
| 1:20 | 16.9 | 24.4 |
| 1:10 | 22.5 | 18.9 |
| 1:5 | 31.1 | 10.2 |
| 1:2.5 | 32.5 | 8.9 |

*Calculated as % of commercial granular soybean lecithin.

The total ethanol extract of commercial granular lecithin was dissolved in 95% ethanol at different concentrations. The mixtures were kept at different temperatures for 24 hours. The yield of the alcohol-soluble fraction can be effected by the solvent ratio and temperature as illustrated in Table V.

TABLE V

FRACTIONAL PRECIPITATION AT DIFFERENT LOW TEMPERATURES AND DIFFERENT SOLVENT RATIOS

| Solvent to Phospholipid Ratio | Temperature (°C.) | Yield (%) of Alcohol-Soluble Fraction* |
|---|---|---|
| 1:40 | $-20$ | 77.1 |
| 1:30 | $-20$ | 69.6 |
| 1:20 | $-20$ | 58.9 |
| 1:10 | $-20$ | 45.7 |
| 1:5 | $-20$ | 24.6 |
| 1:2.5 | $-20$ | 21.5 |
| 1:40 | $-50$ | 58.0 |
| 1:30 | $-50$ | 44.4 |
| 1:20 | $-50$ | 30.7 |
| 1:10 | $-50$ | 25.1 |
| 1:5 | $-50$ | 15.0 |
| 1:10 | $-85$ | 0.24 |
| 1:5 | $-85$ | No Separation |

*Calculated as % of total ethanol extract.

USE OF THE EMULSIFIER

Using the alcohol-soluble fraction produced by the alcohol extraction process of the present invention, oil-in-water emulsions suitable for use in parenteral nutrition are made. The examples set forth below illustrate the use of the alcohol-soluble phospholipid fractions to produce emulsions containing 10% by weight of soybean oil. As illustrated in the following examples, highly stable emulsions may be produced by combining 12 grams of the alcohol-soluble phosholipids with 100 grams of soybean oil and sufficient water to give 1 liter of emulsion i.e., the emulsifier comprises about 1.2% by weight of the emulsion. If desired, a greater (e.g. 2.0%) or lesser (e.g. 0.4%) amount of emulsifier, based on the weight of the total emulsion of the emulsifier, may be used.

The oil-in-water emulsions illustrated in the examples below contain 10% by weight of soybean oil, but the invention is not limited to 10% oil emulsions and emulsions having as much as 30% by weight or more may be produced. Such emulsions may be produced with from about 0.4 to 1.2% by weight of the emulsifier of the present invention, although an increased amount of emulsifier may be desired in the emulsions containing more than 20% by weight of oil.

The oil-in-water emulsions which form a part of the present invention may contain auxiliary materials such as glycerol to adjust the osmotic pressure and caustic to adjust the pH of resulting emulsion. Moreover, vitamins, amino acids, glucose and other carbohydrate substances may be added in accordance with the techniques generally known to the art. Such additives, while useful in producing the oil-in-water emulsions within the scope of the present invention, form no critical part thereof.

The process by which the emulsions are physically formed and the operating conditions for the formation of the emulsions may vary over wide limits. Generally speaking, those techniques which are known to those skilled in the art may be used.

It is clear from the animal tests, illustrated by Examples 2, 3 and 4 that the alcohol-soluble fractions of the present invention are essentially free of toxic components and that some of the alcohol-insoluble soybean phospholipids are poorly tolerated and should be avoided in fat emulsions.

The following examples will serve to illustrate the preparation of several alcohol-soluble soybean phospholipid fractions and the use of such fractions as emulsifiers for making oil-in-water emulsions for parenteral feeding, but it is understood that these examples are set forth merely for illustrative purposes and many other fractions and methods of producing the fractions are within the scope of the present invention. The examples illustrate the formation of 10% oil-in-water emulsions. Those skilled in the art will recognize that oil-in-water emulsions of higher or lower oil content may be similarly prepared.

EXAMPLE 1

Alcohol Fractionation

STEP 1—Seven hundred and fifty g (750) of commecial granular lecithin (ALCOLEC from American Lecithin Company) were dissolved in 1.5 liters of hexane. The solution was poured slowly into 7.5 liters of acetone at 4° C. with agitation. The resulting precipitate was filtered out by the use of a Buchner funnel. The procedure was repeated once.

STEP 2—The precipitate obtained from Step 1 was extracted with 3 liters of 95% ethyl alcohol at 50° C. for 5 minutes. The extraction procedure was repeated once. The residue of the extraction was precipitated once more from acetone to yield 300 g of alcohol-insoluble soybean phospholipids (identified as Product A).

STEP 3—The two ethyl alcohol extracts from Step 2 were combined and were stored at −20° C. for 24 hours. The mixture was then filtered. The precipitate was dissolved in twice its weight of hexane and the solution was poured into ten times the weight of the precipitate of acetone at 4° C. under agitation. The precipitate thus formed was filtered and freed from solvent in a vacuum oven. Fifty-one grams of 1:40 alcohol-insoluble soybean phospholipids were obtained (identified as Product B).

STEP 4—The filtrate from Step 3 was freed of solvent under vacuum to yield 150 g of material. This material was dissolved in 750 ml of 95% ethyl alcohol and the solution was stored at −20° C. for 24 hours. The mixture was then filtered and the precipitate treated in the same manner as described in Step 3 to yield 73 g of 1:5 alcohol-insoluble soybean phospholipids (identified as Product C).

STEP 5—The filtrate from Step 4 was freed from solvent under vacuum and the residue precipitated from acetone to yield 53 g of alcohol-soluble (1:5, −20° C.) soybean phospholipids (identified as Product D).

Figure 1:
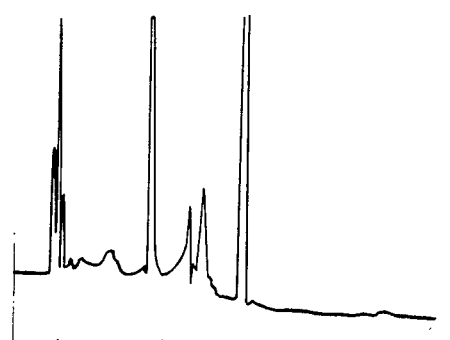
FIG. 1 is a high performance liquid chromatography spectra of a commercial sample of granular soybean lecithin.
Figure 2:
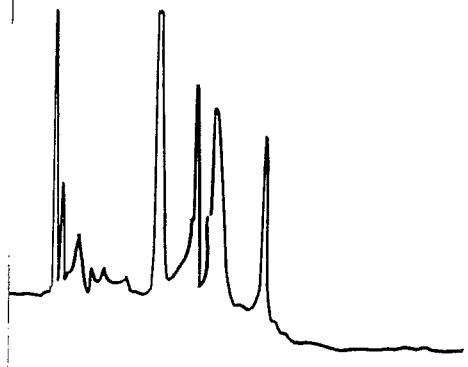
FIG. 2 is high performance liquid chromatography spectra of an alcohol-insoluble fraction remaining after the lecithin of FIG. 1 has been extracted with alcohol.
Figure 3:
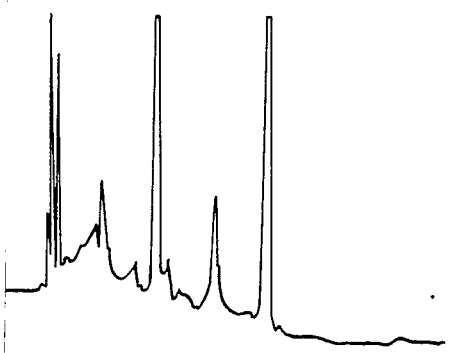
FIG. 3 is a high performance liquid chromatography spectra of an alcohol-insoluble fraction created by a first low temperature fractional precipitation of the alcohol-soluble material of FIG. 2.
Figure 4:
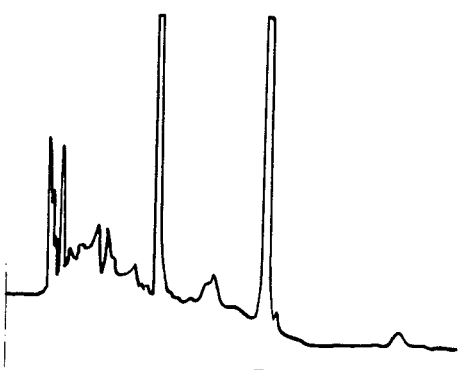
FIG. 4 is a high performance liquid chromatography spectra of an alcohol-insoluble fraction after a second low temperature precipitation at −20° C. of the alcohol-soluble material of FIG. 2.
Figure 5:
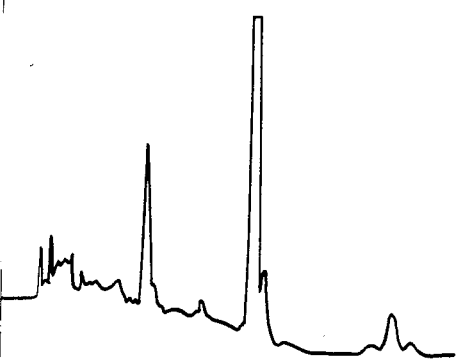
FIG. 5 is a high performance liquid chromatography spectra of an alcohol-soluble fraction remaining after the −20° fractional precipitation.

Analysis of Product of Example 1. The total soybean phospholipids (commercial soybean granular lecithin, ALCOLEC, American Lecithin Co). and its fractions were analyzed by HPLC (High Performance Liquid Chromotography) using a u-Porasil column and a gradient elution from hexane, isopropanol and water (6:8:0.5) to hexane, isopropanol and water (6:8:1.5). An UV detector at 210 nm was used. The chromatograms are as follows:

| Commercial soybean lecithin | FIG. 1 and 6 |
| Product A | FIG. 2 |
| Product B | FIG. 3 |
| Product C | FIG. 4 |
| Product D | FIG. 5 |

The interpretation of the chromatograms are given in Table VI.

TABLE VI

ANALYSIS OF SOYBEAN PHOSPHOLIPID FRACTIONS PRODUCED BY EXAMPLE I

| | Phosphatidyl choline (PC) % | Phosphatidyl ethanolamine (PE) % | PC/PE Mole Ratio | Inositol Phosphatides (PI) % |
|---|---|---|---|---|
| Control (Commercial Lecithin) | 21.8 | 19.9 | 1.02 | 9.2 |
| Product A (Alcohol-Insoluble) | 6.5 | 13.5 | 0.48 | 15.3 |
| Product B (1:40, Alcohol-Insoluble) | 24.5 | 18.3 | 1.34 | 0.8 |
| Product C (1:5, Alcohol-Insoluble) | 44.5 | 12.5 | 3.56 | neg. |
| Product D (Alcohol-Soluble) | 54.8 | 5.3 | 10.34 | neg. |

The same materials were analyzed to determine the fatty acid distribution therein. The fatty acid analysis is shown in Table VII.

TABLE VII

ANALYSIS OF SOYBEAN PHOSPHOLIPID FRACTIONS PRODUCED BY EXAMPLE I FATTY ACID COMPOSITION (% By Weight)

| | C16:0 | C18:0 | C18:1 | C18:2 | C18:3 |
|---|---|---|---|---|---|
| Control (Commercial Lecithin) | 21.36 | 2.48 | 5.49 | 65.33 | 5.35 |
| Product A (Alcohol-Insoluble) | 23.65 | 3.07 | 5.86 | 62.78 | 4.64 |
| Product B (1:40, Alcohol-Insoluble) | 21.19 | 2.71 | 5.48 | 64.30 | 6.21 |
| Product C (1:5, Alcohol-Insoluble) | 17.03 | 2.15 | 6.45 | 69.07 | 5.30 |
| Product D (Alcohol-Soluble) | 10.56 | 1.56 | 5.00 | 78.71 | 4.17 |

The HPLC results show quite clearly that the alcohol soluble soybean phospholipids, Product D (FIG. 5) showed a cleaner chromatogram, as compared to the control (FIG. 1), or Products A through C, (FIGS. 2–4). Integration of the chromatograms showed that Product D (FIG. 5) had a distinctly lower content of inositol phospholipids and a lower content of phosphatidyl ethanolamine, while at the same time displayed a much higher content of phosphatidyl choline. The ratio of phosphatidyl ethanolamine to phosphatidyl choline, as reported in Table VI on a molar basis, clearly shows the distinction between the fractions tested. Product D was also very low in PA and contained reduced amount of glycolipids.

The fatty acid analysis reported in Table VII shows that Product D contained reduced amounts of saturated fatty acids and increased amounts of polyunsaturated fatty acids.

EXAMPLE 2

A series of oil-in-water emulsions were made up using the phospholipids described in Example 1 as the emulsifier and using the quantities of materials set forth in Table VIII. The different batches were identified as Emulsions I, II, III and IV. It should be emphasized that the total commercial soybean lecithin (known as granular lecithin, such as Alcolec) or the commercially available alcohol-soluble fraction of soybean lecithin such as Centrophil S of Central Soya Company, prepared according to the procedure in the literature, when used in fat emulsion for intraveneous feeding will cause undesirable toxic effects such as shown in Emulsions V and VI. Emulsion V is made with commercial granular soybean lecithin. Emulsion VI is made with total ethanol extract of soybean granular lecithin without low temperature fractional precipitation as described in the present invention (1 Kg. of granular soybean lecithin was extracted twice with 4 liters of 95% ethanol at 50° C. for 15 minutes. The extracts were combined and freed from solvent. The residue was dissolved in 926 ml. of hexane and poured into 4.6 liters of acetone to yield 390 g. of precipitate as total ethanol soluble phospholipids.)

TABLE VIII

COMPOSITION OF FAT EMULSIONS WITH VARIOUS FRACTIONS SOYBEAN PHOSPHOLIPIDS, g/l EMULSIONS

| Emulsion No. | I | II | III | IV | V | VI |
|---|---|---|---|---|---|---|
| Soybean Oil | 100 g | 100 g | 100 g | 100 g | 100 g | 100 g |
| Product A | 12 g | | | | | |
| Product B | | 12 g | | | | |
| Product C | | | 12 g | | | |
| Product D | | | | 12 g | | |
| Commercial Granular Soybean Lecithin | | | | | 12 g | |
| Total Ethanol Extract | | | | | | 12 g |
| Glycerol | 22.5 g | 22.5 g | 22.5 g | 22.5 g | 22.5 g | 22.5 g |
| Water sufficient to give | 1 liter | 1 liter | 1 liter | 1 liter | 1 liter | 1 liter |

To test nutritional tolerance and subchronic toxicity, four weeks intravenous administration was given to male Sprague-Dawley rats. The method employed is a standard technique which has been described in detail in the prior art and is widely used and accepted. The results are shown in Table IX.

TABLE IX

STUDIES WITH FAT EMULSIONS CONTAINING VARIOUS SOYBEAN PHOSPHOLIPIDS Administration was 9 g TG/kg and 1.1 g PL/kg and day for 28 days.
Organ weights (g/kg) and growth (g/day)
Values are given as mean with four animals in each group

| | PHOSPHOLIPID TESTED | | | | | |
|---|---|---|---|---|---|---|
| Organs | Product A Emulsion I | Product B* Emulsion II | Product C Emulsion III | Product D Emulsion IV | Commercial Granular Lecithin Emulsion V | Total Ethanol Extract Emulsion VI |
| Liver (g/kg) | 67.9 | 81.2 | 62.5 | 45.1 | 73.8 | 64.6 |
| Spleen (g/kg) | 5.56 | 4.76 | 7.16 | 4.03 | 8.28 | 6.83 |
| Kidneys (g/kg) | 7.64 | 8.88 | 7.92 | 7.42 | 8.15 | 10.23 |
| Lungs (g/gk) | 5.79 | 8.44 | 5.45 | 4.52 | 6.63 | 6.07 |
| Hearts (g/kg) | 4.26 | 5.29 | 4.18 | 3.82 | 6.64 | 3.24 |
| Thymus (g/kg) | 1.12 | 0.64 | 0.98 | 2.02 | 0.70 | 1.10 |
| Bodyweight at end of 28 days (g) | 238.5 | 192.1 | 248.9 | 312.7 | 207.0 | 215.6 |
| Growth 0-28 days (g/day) | 0.97 | −2.71 | 1.31 | 3.43 | 0.23 | .48 |

*Did not complete the test period, sacrificed after 15 infusion days.

The foregoing tests demonstrate that the emulsion made with the fraction designated Product A shows clear signs of lower tolerance with very poor growth and marked increases in organ weights for liver, spleen, lungs, and heart. The hematology revealed clear and severe anemia. Histology revealed degenerative changes in heart and thymus.

The emulsion made with the fraction designated Product B showed very grave signs of toxicity along with pronounced weight loss. Liver cell necrosis was found and clear degenerative changes were seen in heart and thymus. Blood showed a severe lipemia.

The emulsion made with the fraction designated Product C showed diminished growth rate compared to the control group and several organs were severely increased in weight. (Histology more or less normal.)

The emulsion made with the emulsifier of the present invention, i.e., the alcohol-soluble fraction, Product D, showed normal growth as compared to the growth achieved with an oral control. All organ weights and histopathology were normal as were the blood analysis, enzymes and lipids. The levels of cholesterol and phospholipids are clearly lower as compared to commercially marketed oil-in-water emulsions based on soybean oil and phospholipid emulsifiers derived from eggs.

Emulsion made with granular lecithin (Emulsion V) and total ethanol extract (Emulsion VI) showed all the undesirable effects seen with Products A, B and C.

EXAMPLE 3

A Comparison of Fat Emulsion with Purified Soybean Phospholipids (Product D) and Commercial Fat Emulsions We have compared our fat emulsion with alcohol-soluble soybean phospholipids with commercial fat emulsions in a biological tolerance test.

The biological test in animals has been described under Example 2. In this study we administered 180 ml fat emulsion per kg bodyweight and day. The infusions were intended to last for 28 days.

Table X shows the composition of commercial fat emulsions, Lipofundin S., Lipiphysan and Product D. The results are presented in Table XI.

TABLE X

COMPOSITION OF FAT EMULSIONS (g/l)

| | Lipofundin S | Lipiphysan | Fat Emulsion With Product D |
|---|---|---|---|
| | 10% | 10% | |
| Soybean oil | 100 g | | 100 g |

TABLE X-continued

| COMPOSITION OF FAT EMULSIONS (g/l) | | | |
|---|---|---|---|
| | Lipofundin S 10% | Lipiphysan 10% | Fat Emulsion With Product D |
| Cottonseed oil | | 100 g | |
| Soybean Phospholipid | 7.5 g | 15 g | |
| Product D | | | 12 g |
| Glycerol | | | 22.5 g |
| Sorbitol | | 50 g | |
| Xylitol | 50 g | | |
| DL-alpha-tocopherol | | 0.5 g | |
| Aq. dest. up to | 1 liter | 1 liter | 1 liter |

TABLE XI

STUDIES WITH FAT EMULSIONS CONTAINING SOYBEAN PHOSPHOLIPIDS.
LIPOFUNDIN S, LIPIPHYSAN AND PRODUCT D.
Administration of 18 g TG/kg and day, intended for 28 days
Organ weights and growth

| | Lipofundin S n = 4 | *Lipiphysan n = 4 | Product D n = 8 |
|---|---|---|---|
| Liver g/kg | 62.9 | 73.7 | 49.5 |
| Spleen g/kg | 4.79 | 4.51 | 4.10 |
| Kidneys g/kg | 7.27 | 9.30 | 7.30 |
| Lungs g/kg | 5.42 | 7.28 | 4.50 |
| Heart g/kg | 5.17 | 5.10 | 4.00 |
| Thymus g/kg | 0.55 | 0.76 | 1.50 |
| Bodyweight at end (g) | 269.2 | 179.9 | 305.5 |
| Growth Week 0-4 (g/day) | 1.89 | *−0.88 | 3.55 |

*Administration lasted 7 days, then animals were sacrificed for humane reasons.

The results clearly indicate highly undesirable effects of Lipiphysan where the infusion had to be terminated after 7 days of infusions. These animals had severely changed organs due to given fat emulsion. Also Lipofundin S showed undesirable effects with lowered growth, increased organ weights as well as histological changes.

Fat emulsion with product D phospholipids showed a good and normal tolerance in all studied parameters.

We thus demonstrate, at this high dose level, a clear difference between various fat emulsions containing soybean phospholipids.

Our product D showed to be superior compared with commercially available fat emulsions containing soybean phospholipids.

Instead of using granular soybean lecithin as the starting material, the alcohol soluble fraction of soybean lecithin of our invention can also be prepared from wet gum of soybean processing. In this manner, an added advantage is observed as the product has a lower content of lysophaphatidyl choline as shown in Example 4.

EXAMPLE 4

1425 grams of fresh wet gum, obtained by normal commercial water degumming of crude soybean oil were used. The wet gum contained 28.9% of water. It was dissolved in 2850 ml. of hexane and poured into 14.2 liters of acetone at room temperature. The precipitate was filtered and washed with acetone until the washing was colorless.

The precipitate was extracted three times with five times the volume of the weight of the phospholipids of 95% ethanol and then extracted once with 2.5 times of 95% ethanol. The extracts were combined and stored at −20° C. for 24 hours. The precipitate was separated by filtration. The solvent in the filtrate was partially removed under vacuum to a concentration of 5 volumes of solvent to 1 part by weight of phospholipids. The mixture was stored at −20° C. for 24 hours. The precipitate was separated by filtration. The filtrate was freed of solvent under vacuum at room temperature to obtain 86.1 g. of the product designated "PFWG".

Product PFWG, the alcohol soluble fraction prepared according to the present invention as analyzed by HPLC showed 76.8% of phosphatidyl choline. It contained 1.2% of lysophosphatidyl choline, which is significantly lower than a similar product prepared with commercial granular lecithin as the starting material. For example, Product D, by the same analysis, showed 5.8% of lysophosphatidyl choline.

Fat emulsions having 20% by weight of soybean oil were made with 1.2% of the soybean phospholipids as described previously. The biological tolerance tests of these emulsions were done with rats, as described previously. The results are shown in Table XII:

TABLE XII

COMPARISON OF BIOLOGICAL TOLERANCE OF ALCOHOL SOLUBLE FRACTION OF SOYBEAN PHOSPHOLIPIDS PREPARED FROM WET GUM (PFWG) WITH OTHER PRODUCTS.

| Phospholipids Tested Emulsion | Example 4 Product PFWG I | Epikuron 1%* II | Ethanol Insoluble (1:40, −20° C., 24 hrs.) Soybean Phospholipids III |
|---|---|---|---|
| Liver (g/kg) | 50.3 | 70.1 | 70.9 |
| Spleen (g/kg) | 5.90 | 10.03 | 5.08 |
| Kidneys (g/kg) | 7.70 | 10.01 | 9.70 |
| Lungs (g/kg) | 4.70 | 6.47 | 6.91 |
| Heart (g/kg) | 4.13 | 5.10 | 4.60 |
| Thymus (g/kg) | 1.52 | 0.64 | 0.94 |
| Body weight at the end of 28 days (g) | 308 | 249 | Animal died |

*Commercial product of soybean phospholipids by Lucas Meyer, containing 68–72% of phosphatidyl choline.

The example given below illustrates a modified extraction technique which may be used to produce a sugar free phospholipid.

EXAMPLE 5

460 Grams of commercial granular soybean lecithin (Centrolex from Central Soya Company) is dissolved in 920 ml of hexane and poured into 4.6 l of acetone at room temperature. The precipitate was filtered and washed with acetone until the washing is colorless. The precipitate was extracted three times with five times its weight in volume of 95% ethanol and once more with 2.5 times its weight in volume of 95% ethanol at room temperature. All the extracts were combined and the solvent removed under reduced pressure at room temperature.

The residue was dissolved in five times its weight of pentane and the solution was extracted twice with five times in volume of the weight of the residue of 60% ethanol. The pentane solution is then freed from solvent under vacuum at room temperature. The residue was submitted to the low temperature fractional separation method as described previously to yield 61.2 grams of sugar-free soybean phospholipids which are soluble in 95% ethanol at −20° C. at a ratio of 1:5. The product, called "Product SFSP", is useful in the preparation of oil-in-water emulsions, as illustrated above.

The forms of invention herein shown and described are to be considered only as illustrative. It will be apparent to those skilled in the art that numerous modifications may be made therein without departure from the spirit of the invention or the scope of the appended claims.

What is claimed is:

1. A soybean phospholipid emulsifier adapted for use in nutritive oil-in-water emulsions suitable for parenteral administration, said emulsifier comprising a fraction of soybean lecithin produced by:
   extracting soybean lecithin with a lower alkyl alcohol having up to 3 carbon atoms;
   chilling the filtrate of said extraction to between about −20° and −85° C. and at alcohol concentrations between 2.5:1 and 40:1, solvent:phospholipid, for a time effective to precipitate insoluble materials comprising toxic materials; and
   recovering the soluble soybean lecithin fraction from the solution as the emulsifier.

2. A soybean phospholipid emulsifier as described in claim 1, wherein the soybean lecithin is "wet gum" obtained from degumming of crude vegetable oils.

3. A soybean phospholipid emulsifier as described in claim 1, wherein the lower alkyl alcohol comprises ethyl alcohol.

4. A soybean phospholipid emulsifier as described in claim 1, wherein the precipitation is carried out at about −20° C.

5. A soybean phospholipid emulsifier as described in claim 1, wherein the precipitation is carried out at an alcohol concentration of about 5 to 1.

6. A soybean phospholipid emulsifier adapted for use in nutritive oil-in-water emulsions suitable for parenteral administration, said emulsifier comprising a lower alkyl alcohol-soluble fraction of soybean lecithin produced by removing insolubles precipitated at temperatures between about −20° C. and −80° C. and alcohol to phospholipid ratios between 2.5:1 and 40:1, said fraction comprising about 55% by weight of phosphatidyl choline, about 5% by weight of phosphatidyl ethanol amine and essentially free of inositol phospholipids and phosphatidic acid.

7. A soybean phospholipid emulsifier as described in claim 6, wherein the alcohol-soluble fraction contains about 12% by weight of saturated fatty acids and about 79% by weight of polyunsaturated acids.

8. A method of preparing a soybean phospholipid emulsifier adapted for use in a nutritive oil-in-water emulsion suitable for parenteral administration comprising extracting soybean lecithin a plurality of times with a lower alkyl alcohol having up to 3 carbon atoms, precipitating the insolubles from each filtrate at temperatures between about −20° and −85° C. and alcohol concentrations between about 2.5 and 40 liters of alcohol per kilogram of lecithin for a time sufficient to precipitate toxic materials, and recovering the alcohol-soluble fraction as the emulsifier.

9. A method as described in claim 8 wherein the lower alkyl alcohol used for one extraction consists essentially of ethyl alcohol.

10. A method as described in claim 9 wherein the lower alkyl alcohol for all extractions consists essentially of ethyl alcohol.

11. A method as described in claim 8 wherein the first extraction comprises mixing lecithin with alcohol at about 50° C.

12. A method as described in claim 11 wherein the alcohol-soluble fraction is separated from the insoluble fractions by chilling the alcohol-phosphatide mixture to about −20° C. followed by filtration.

13. A method as described in claim 11 wherein the insolubles are precipitated using an alcohol concentration of about 5 liters of alcohol to 1 kilogram of lecithin.

14. A nutritive oil-in-water emulsion suitable for parenteral administration comprising soybean oil, an emulsifier for said oil, and water:
   said emulsifier consisting essentially of a fraction of soybean lecithin produced by:
   extracting a weight of soybean lecithin with a lower alkyl alcohol having up to 3 carbon atoms, the volume of alcohol being a ratio of at least 2 liters of alcohol for each kilogram of lecithin;
   chilling the filtrate of said extraction to between about −20° and −85° C. and at alcohol concentrations between 2.5:1 and 40:1, solvent:phospholipid, for a time effective to precipitate insoluble materials comprising toxic materials; and
   recovering the soluble soybean lecithin fraction from the solution as the emulsifier.

15. A nutritive oil-in-water emulsion as described in claim 14, wherein the lower alkyl alcohol comprises ethyl alcohol.

16. A nutritive oil-in-water emulsion as described in claim 14, wherein the precipitation is carried out at about −20° C.

17. A nutritive oil-in-water emulsion as described in claim 14, wherein the precipitation is carried out at an alcohol concentration of about 5 to 1.

18. A nutritive oil-in-water emulsion as described in claim 14 which comprises 10–30% by weight of soybean oil.

19. A nutritive oil-in-water emulsion as described in claim 14 which comprises from about 0.4% to 2% by weight of said emulsifier.

20. A nutritive oil-in-water emulsion suitable for parenteral administration comprising soybean oil, an emulsifier for said vegetable oil, and water:
   said emulsifier comprising a lower alkyl alcohol-soluble fraction of soybean lecithin produced by removing insolubles precipitated at temperatures between about −20° C. and −80° C. and alcohol to phospholipid ratios between 2.5:1 and 40:1 said alcohol having no more than 3 carbon atoms, said fraction comprising about 55% by weight of phosphatidyl choline, about 5% by weight of phosphatidyl ethanol amine and essentially free of inositol phospholipids and phosphatidic acid.

* * * * *